(12) United States Patent
Thomson

(10) Patent No.: US 7,171,257 B2
(45) Date of Patent: Jan. 30, 2007

(54) APPARATUS AND METHOD FOR RADIOSURGERY

(75) Inventor: Euan Thomson, Los Gatos, CA (US)

(73) Assignee: Accuray Incorporated, Sunnyvale, CA (US)

( * ) Notice: Subject to any disclaimer, the term of this patent is extended or adjusted under 35 U.S.C. 154(b) by 209 days.

(21) Appl. No.: 10/743,502

(22) Filed: Dec. 22, 2003

(65) Prior Publication Data

US 2004/0267113 A1 Dec. 30, 2004

Related U.S. Application Data

(60) Provisional application No. 60/477,573, filed on Jun. 11, 2003, provisional application No. 60/477,551, filed on Jun. 11, 2003.

(51) Int. Cl.
*A61B 5/05* (2006.01)
*G21K 5/10* (2006.01)

(52) U.S. Cl. .................... 600/427; 600/429; 378/69

(58) Field of Classification Search ............... 600/425, 600/427, 428
See application file for complete search history.

(56) References Cited

U.S. PATENT DOCUMENTS

| 4,452,252 | A | * | 6/1984 | Sackner ................. 600/484 |
|---|---|---|---|---|
| 4,583,538 | A | | 4/1986 | Onik et al. |
| 5,067,981 | A | | 11/1991 | Hooykaas |
| 5,207,223 | A | | 5/1993 | Adler |
| 5,222,499 | A | | 6/1993 | Allen et al. |
| 5,447,154 | A | | 9/1995 | Cinquin et al. |
| 5,457,728 | A | * | 10/1995 | Whiting et al. ........... 378/98.2 |
| 5,537,452 | A | | 7/1996 | Shepherd et al. |
| 5,588,430 | A | | 12/1996 | Bova et al. |
| 5,622,187 | A | | 4/1997 | Carol |
| 5,727,554 | A | | 3/1998 | Kalend et al. |
| 5,797,849 | A | | 8/1998 | Vesely et al. |

(Continued)

FOREIGN PATENT DOCUMENTS

WO  WO 2005/000102 A2  1/2005

OTHER PUBLICATIONS

Achim Schweikard, et al. "Robotic Motion Compensation For Respiratory Movement During Radiosurgery", Computer Aided Surgery, 5:263-277 (2000).

(Continued)

*Primary Examiner*—Brian L. Casler
*Assistant Examiner*—Sanjay Cattungal
(74) *Attorney, Agent, or Firm*—Blakely, Sokoloff, Taylor & Zafman LLP

(57) ABSTRACT

A method and system is presented for treating moving target regions in a patient's anatomy by creating radiosurgical lesions. The method includes determining a pulsating motion of a patient separately from a determining of a respiratory motion, and directing a radiosurgical beam, from a radiosurgical beam source, to a target in the patient based on the determining of the pulsating motion. Directing the radiosurgical beam to the target may include creating a lesion in the heart to inhibit atrial fibrillation. The method may further include determining the respiratory motion of the patient, and compensating for movement of the target, due to the respiratory motion and the pulsating motion of the patient, in the directing of the radiosurgical beam based on the determining of the respiratory motion and the determining of the pulsating motion.

27 Claims, 5 Drawing Sheets

U.S. PATENT DOCUMENTS

| | | | |
|---|---|---|---|
| 5,901,199 A | * | 5/1999 | Murphy et al. ............... 378/65 |
| 5,971,997 A | | 10/1999 | Guthrie et al. |
| 6,006,126 A | | 12/1999 | Cosman |
| 6,076,005 A | | 6/2000 | Sontag et al. |
| 6,120,453 A | | 9/2000 | Sharp |
| 6,144,875 A | | 11/2000 | Schweikard et al. |
| 6,314,312 B1 | * | 11/2001 | Wessels et al. ............. 600/427 |
| 6,501,981 B1 | | 12/2002 | Schweikard et al. ........ 600/427 |
| 6,889,695 B2 | * | 5/2005 | Pankratov et al. .......... 128/898 |
| 2002/0193685 A1 | * | 12/2002 | Mate et al. ................. 600/424 |
| 2004/0131150 A1 | | 7/2004 | Pankratov et al. |

OTHER PUBLICATIONS

Toni Neieu, et al., "Synchronizded Moving Aperture Radiation Therapy (SMART); Average Tumor Trajectory For Lung Patients", Phys. Med. Biol. 48 (2003) 587-598.

R. Ginhoux, J. A. Gangloff, M. F. de Mathellin, LSIIT UMR 7005 CNRS, Louis Pasteur University, Strasboug I, Bd Sebastein Brant, BP 10413, F-67412 Illkirch Cedex, France / L. Soler, Mara M. Arenas Sanchez and J. Marescaux, IRCAD / EITS, European Institute of Telesurgery, University Hospital of Strasbourg, 1, place de l'hopital, F-67091 Strasbourg Cedex, France, Beating Heart Tracking In Robotic Surgery Using 500 Hz Visual Servoing, Model Predictive Control And An Adaptive Observer.

Gregory C. Sharp et al, "Prediction Of Respiratory Tumour Motion For Real-Time Image-Guided Radiotherapy", Phys. Med. Biol. 49 (2004) 425-440.

"International Search Report", International Searching Authority, PCT/US04/18742, Oct. 25, 2005, 4 pages.

"Written Opinion of the International Searching Authority", International Searching Authority, PCT/US04/18742, Oct. 25, 2005, 6 pages.

* cited by examiner

APPARATUS AND METHOD FOR
RADIOSURGERY

CROSS-REFERENCE TO RELATED APPLICATIONS

This application claims the benefit of U.S. Provisional Application No. 60/477,573, filed Jun. 11, 2003, and U.S. Provisional Application No. 60,477,551, filed Jun. 11, 2003.

FIELD OF THE INVENTION

The present invention relates to creation of lesions whose positions are significant during the course of treatment, such as lesions located on the heart, or on organs close to the heart. More particularly, the invention relates to a method and system for treating cardiac-related diseases, and for creating lesions on anatomical regions that undergo motion, such as motion due to pulsating arteries.

BACKGROUND

A number of medical conditions involve creating lesions whose positions are significant during the course of treatment, such as lesions that are located on the heart or on other organs close to the heart. In many cases, it is necessary to create lesions on anatomical regions that undergo rapid motion, for example motion due to pulsating arteries. Traditionally, the creation of such lesions or moving anatomical regions has required invasive surgery, such as open heart surgery for cardiac-related treatments.

As one example, atrial fibrillation is a medical condition characterized by an abnormally rapid and irregular heart rhythm, because of uncoordinated contractions of the atria (i.e. the upper chambers of the heart.) A normal, steady heart rhythm typically beats 60–80 times a minute. In cases of atrial fibrillation, the rate of atrial impulses can range from 300–600 beats per minute (bpm), and the resulting ventricular heartbeat is often as high as 150 bpm or above. A curative surgical treatment for atrial fibrillation that is known in the art is the so called "maze procedure," which is an open heart procedure involving incisions and ablations of tiny areas of the atria. The surgeon makes a plurality of incisions or lesions in the atria, so as to block the re-entry pathways that cause atrial fibrillation. Upon healing, the lesions form scar tissue, which electrically separate portions of the atria, and interrupt the conduction of the abnormal impulses. While this procedure can be effective, with a high cure rate, the procedure is long and difficult to perform.

In general, possible complications of an invasive surgery are significant, and include stroke, bleeding, infection, and death. One technique for avoiding the complications of invasive surgery is radiosurgery, which is recognized as being an effective tool for noninvasive surgery. Radiosurgery involves directing radiosurgical beams onto target regions, in order to create lesions to necrotize tumorous tissue. The goal is to apply a lethal or other desire amount of radiation to one or more tumors, or to other desired anatomical regions, without damaging the surrounding healthy tissue. Radiosurgery therefore calls for an ability to accurately direct the beams upon a desired target, so as to deliver high doses of radiation in such a way as to cause only the target to receive the desired dose, while avoiding critical structures. The advantages of radiosurgery over open surgery include significantly lower cost, less pain, fewer complications, no infection risk, no general anesthesia, and shorter hospital stays, most radiosurgical treatments being outpatient procedures.

In order to avoid the disadvantages of invasive surgery, such as the open heart surgical procedure described above, it is desirable to provide a method and system for using radiosurgery to treat diseases that require the creation of lesions in specifically targeted anatomical regions. These anatomical regions may be located on a beating heart wall of a patient, or on organs near the heart. Alternatively, these anatomical regions may be located in other places within the patient's anatomy that undergo motion, e.g. due to pulsating arteries.

For these reasons, is desirable to provide a method and system in radiosurgery for precisely applying radiosurgical beams onto these moving anatomical regions of a patient.

SUMMARY OF THE INVENTION

The present invention is directed to the radiosurgical creation of lesions whose positions are significant during the course of treatment, and to the radiosurgical treatment of anatomical regions that undergo motion. For example, these lesions and/or anatomical regions may be located on beating heart walls, or on organs near the heart, or on pulsating arteries.

In accordance with one embodiment of the invention, a method is presented for treating a moving target in a patient by applying to the target one or more radiosurgical beams generated from a radiosurgical beam source. The method includes generating a pre-operative 3D scan of the target and of a region surrounding the target, the 3D scan showing the position of the target relative to the surrounding region. Based on the pre-operative 3D scan, a treatment plan is generated, which defines a plurality of radiosurgical beams appropriate for creating at least one radiosurgical lesion on one or more targets within the patient.

In a preferred embodiment of the invention, the target undergoes motion. For example, the motion may be caused by heart beat and/or respiration. The movement of the target is detected and monitored. In near real time, the position of the moving target at a current time is determined, and the difference between the position of the target at the current time, as compared to the position of the target as indicated in the 3D scan, is determined. In near real time, the relative position of the radiosurgical beam source and the target is adjusted, in order to accommodate for such a difference in position. This process is repeated continuously throughout the treatment period.

In one embodiment of the present invention, a composite motion (caused by respiration and heartbeat, by way of example) of the target is tracked, and one or more signals are generated that are representative of the motion of the target. For example, a breathing sensor and a heart beat monitor may be used to detect the respiration and cardiac pumping of the patient. Information from the breathing sensor and the heartbeat monitor is then combined, in order to enable the surgical x-ray source to track the position of the target as it moves due to respiration and cardiac pumping, and to generate signals representative of the position of the moving target.

The signal that represents the composite motion of the target is then processed to generate two separate signals, each signal being characterized by the frequency of the individual motions that make up the composite motion. In an embodiment of the invention in which the composite motion is due to respiration combined with heart beat, the first signal is substantially characterized by the frequency (F1) of the respiratory cycle of the patient, and the second signal is substantially characterized by the frequency (F2) of the heartbeat cycle of the patient.

A correction factor is then computed for each signal separately. The correction factor for the first signal is effective to compensate for the movement of the target due to respiration of the patient. The patient's respiratory motion is characterized by a respiratory cycle. The correction factor for the second signal is effective to compensate for the movement of the target due to the cardiac pumping motion in the patient. The cardiac motion of the patient is characterized by a heartbeat cycle. Both correction factors are applied to a controller that controls the position of the radiosurgical beam source, to modify the relative position of the beam source and the target, in order to account for the displacement of the target due to its composite motion. The surgical x-ray beams are applied from the modified position of the beam source in accordance with the treatment plan, so that the lesions are formed at the desired locations in the patient's anatomy. The processes of tracking the motion of the target, computing the resulting difference in target position, and adjusting the relative position of the beam source and the target accordingly, are repeated continuously throughout the treatment.

In use, an observer would see the x-ray source move seemingly in synchronization with the chest wall (i.e. with the respiration), but also including short pulsating motion corresponding to the heart beat cycle. The x-ray source tracks the movement caused by both respiration and heartbeat, while delivering x-rays to the target in accordance with the treatment plan.

In one form of the invention, using techniques similar to those disclosed in U.S. Pat. No. 6,501,981 (the "'981 patent")(owned by the assignee of the present application and hereby incorporated by reference in its entirety), the motion of tissue at or near the target is determined. For example, a look-up table of positional data may be established for a succession of points along the each of the respiratory cycle and the heartbeat cycle. Motion points for the respiratory cycle include position information obtained in response to both respiration and heartbeat of the patient. Positional information for the heartbeat cycle can be obtained through imaging of the tissue while the patient is holding his breath. A table ("table 2") containing this positional information can provide the basis for first signal. The second signal, on the other hand, can be obtained by subtracting data from the table for the heartbeat cycle (obtained by having the patient hold his breath) from the data from the composite motion (formed of both respiration and heartbeat), since the resulting table ("table 1") corresponds to motion caused substantially only by respiration. Positional changes for the x-ray source can be applied based on superposition of data from table 1 and table 2.

DETAILED DESCRIPTION

In the present invention, the techniques of radiosurgery are used to treat target tissue by creating radiosurgical lesions. These lesions are created in anatomical target regions located in places that undergo constant motion, such as the heart walls of a beating heart. The motion of the target, due to respiration and heart beat, is continuously tracked during treatment, so that the radiosurgical beams remain properly directed onto the desired target regions in the patient's anatomy.

Figure 1:
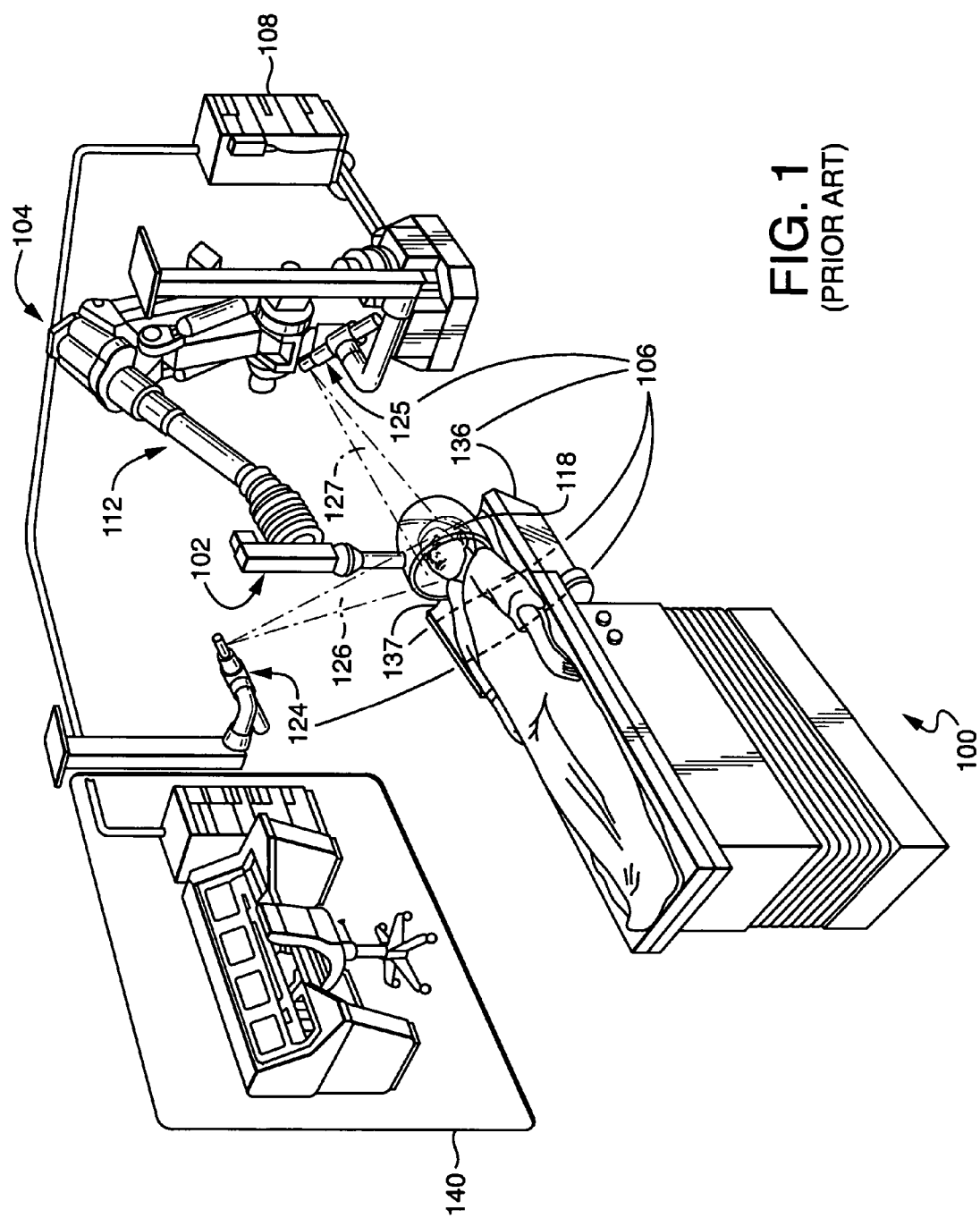
FIG. 1 illustrates a radiosurgical treatment system, known in the prior art.

FIG. 1 illustrates a radiosurgical treatment system, known in the art. The radiosurgery system 100 shown in FIG. 1 may, for example, represent the CyberKnife® system developed by Accuray, Inc. In overview, the conventional radiosurgery system 100 includes a radiosurgical beaming apparatus 102; a positioning system 104; imaging means 106; and a controller 108. The system 100 may also include an operator control console and display 140. The radiosurgical beaming apparatus 102 generates, when activated, a collimated radiosurgical beam (consisting of x-rays, for example). The cumulative effect of the radiosurgical beam, when directed to the target, is to necrotize or to create a lesion in a target 118 within the patient's anatomy. By way of example, the positioning system 104 is an industrial robot, which moves in response to command signals from the controller 108. The beaming apparatus 102 may be a small x-ray linac mounted to an arm 112 of the industrial robot 104. The imaging means 106 may be an x-ray imaging system, having a pair of x-ray sources 124 and 125 for generating diagnostic imaging beams 126 and 127, and x-ray image detectors 136 and 137.

In the prior art system 100, the imaging means 106 generates real-time radiographic images of the anatomical region containing the target, by transmitting one or more imaging beams through the target. The controller 108 determines the real-time location of the target, by comparing the real-time radiographic image with pre-operative CT (or MRI) scans of the target that have been stored within the computer. The positioning system 104 manipulates the position of the radiosurgical beam, in response to control commands from the controller 108, so as to keep the radiosurgical beam properly directed to the target.

In order to account for the motion of a moving target, for example due to respiration of the patient, patients have typically been advised to hold their breath while being scanned by the CT scanner, prior to treatment. In this way, the moving patient is fixed, and therefore the scan does not have any motion artifacts. More recently, new radiosurgical devices, such as the CyberKnife® have been employing new technologies for treating moving targets. For example, Accuray recently revealed a new product, Synchrony®, which is Accuray's new system for delivering dynamic radiosurgery to tumors that move with respiration. The Synchrony® system is described in U.S. Pat. No. 6,501,981 (the "'981 patent"), entitled "Apparatus And Method For Compensating For Respiratory And Patient Motions During Treatment," which issued on Dec. 31, 2002 to A. Schweikard and John R. Adler. The '981 patent is owned by the assignee of the present application, and is hereby incorporated by reference in its entirety. The Synchrony® system precisely tracks tumors in or near the lungs as they move, enabling highly directed beams of radiation to destroy the tumors with minimal damage to adjacent normal tissue. In particular, the Synchrony® system records the breathing movements of a patient's chest, and combines that information with sequential x-ray pictures of tiny markers inserted inside or near the tumor. In this way, the Synchrony® system enables precise delivery of radiation during any point in the respiratory cycle.

Figure 2A:
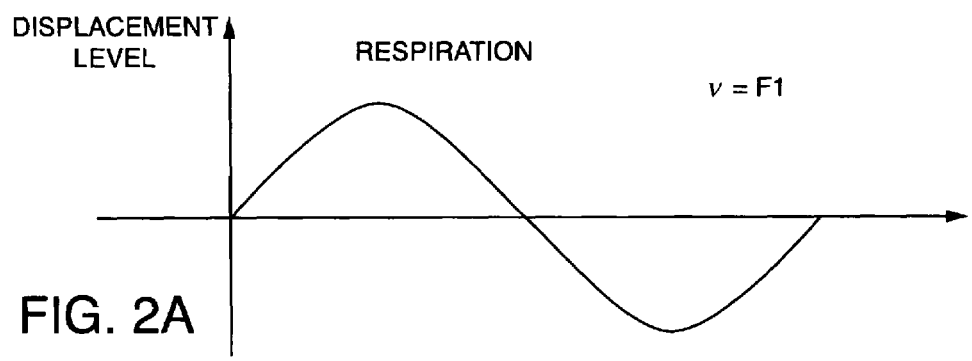
FIGS. 2A, 2B, and 2C depicts the frequency patterns of the motion of a target region of the patient, caused by respiratory motion (in FIG. 2A), cardiac pumping motion (in FIG. 2B) and by a composite motion due to the combination of the respiratory motion and the cardiac pumping motion (in FIG. 2C).
Figure 2B:
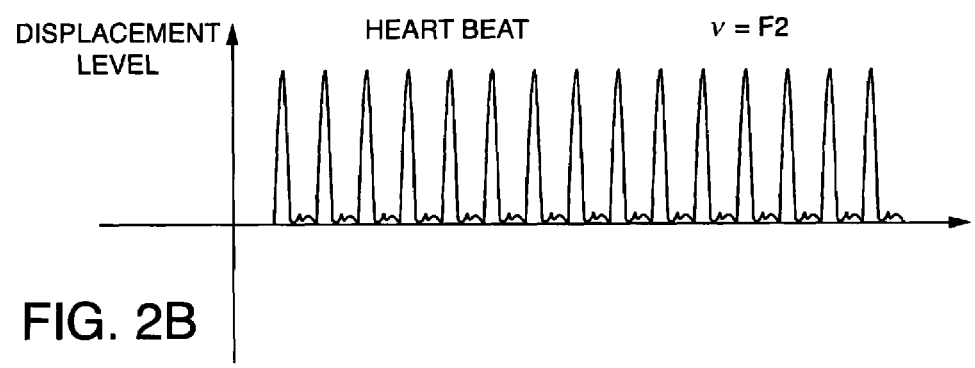
Figure 2C:
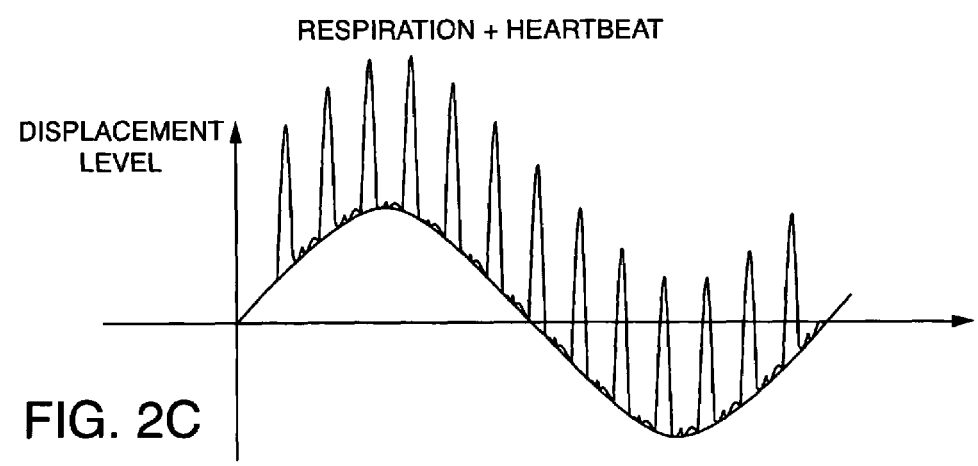

In a preferred embodiment of the present invention, the motion of the target (located e.g. on the atrial walls of a beating heart) is a composite motion caused by at least two factors: a) respiratory movement of the patient; and b) rapid pulsation or pumping motion of the heart of the patient. FIGS. 2A, 2B, and 2C depict the frequency patterns of the motion of a target within the patient, caused by respiratory motion (in FIG. 2A), cardiac pumping motion (in FIG. 2B) and by a composite motion due to the combination of the respiratory motion and the cardiac pumping motion (in FIG. 2C). The target may be located on a heart wall, or on other moving regions of the patient's anatomy. The respiratory motion is characterized by a respiratory cycle, whose frequency (F1) is about an order of magnitude lower, compared to the frequency (F2) of the cardiac pumping motion. The composite or resultant motion of the target, as illustrated in FIG. 2C, is simply a superposition of the respiratory motion (shown in FIG. 2A) and the cardiac pumping motion (shown in FIG. 2B).

Figure 3A:
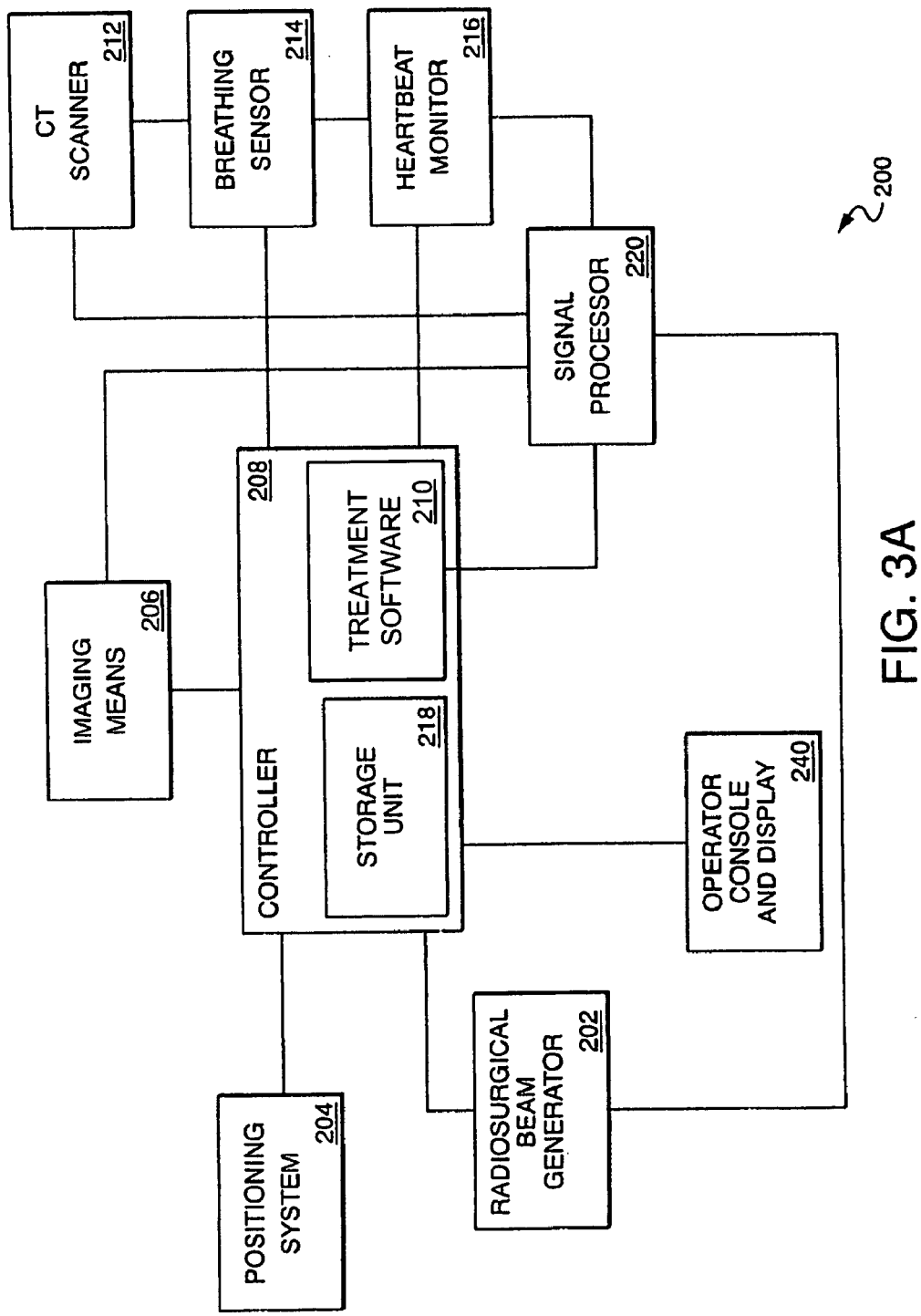
FIG. 3A provides a schematic block diagram of a radiosurgical system for treating a target region by creating radiosurgical lesions, constructed in accordance with one embodiment of the present invention.

FIG. 3A provides a schematic block diagram of a radiosurgical system 200, constructed in accordance with one embodiment of the present invention, for treating a patient by creating radiosurgical lesions in moving anatomical regions. The description of FIG. 3A will focus on cardiac-related treatments, although the scope of the present invention is not limited to cardiac-related treatments, but rather encompasses the treatment of any anatomical region that undergoes motion, for example motion due to pulsating arteries.

The system 200 includes a CT scanner 212 for generating CT scan data representative of a pre-operative 3-D diagnostic image of the anatomical target, and surrounding tissue. The target is located in those areas in which the formation of lesions would be therapeutic. For example, in the case of atrial fibrillation, the target is located in those areas in which the formation of lesions would cure atrial fibrillation by properly directing electrical impulses to the AV node and onto the ventricles. Because the target undergoes motion due to respiration and cardiac pumping, a plurality of fiducials may be implanted in the atria near the target, so that the pre-operative diagnostic image shows the position of the target in reference to the fiducials. The pre-operative image is a static image, or "snapshot", of the target and surrounding tissue.

The system 200 includes a radiosurgical beam source 202 for generating one or more radiosurgical beams, preferably x-rays. The cumulative effect of applying the radiosurgical x-ray beams during the treatment period is to create at least one lesion in the target, so that the desired clinical purpose can be accomplished. In the illustrated embodiment, as in the prior art, the radiosurgical beam source 202 is a small x-ray linac. The system 200 also includes a surgical beam positioning system 204. As in the prior art, the positioning system 204 in the illustrated embodiment is an industrial robot, which moves in response to command signals from a central controller 208. The x-ray linac 202 is mounted to an arm of the industrial robot 204. It should be noted that other types of beam source 202 and positioning system 204 known in the art may be used, without departing from the scope of the present invention.

The central controller 208 is preferably a multi-processor computer. The controller 208 may also include a storage unit 218 (for example, for storing the pre-operative CT scan data), and an operator console and display 240. The controller 208 preferably has a plurality of processing or controller units, including, inter alia: 1) treatment software 210 for generating, based on the CT scan data generated by the CT scanner 212, a treatment plan that defines a plurality of x-ray beams appropriate for creating one or more lesions in an anatomical target region in the heart; and 2) a controller unit 300 for sending command signals to the positioning system 204 (i.e. the robot), so as to adjust the relative position of the beam source 202 and the target. The treatment plan contains information regarding the number, intensities, positions, and directions of the x-ray beams that are effective to create at least one radiosurgical lesion.

The system 200 further includes imaging means 206 for generating x-ray radiographs of the target. The imaging means 206 typically includes a pair of x-ray sources for generating x-ray imaging beams, and an x-ray imaging system. The x-ray imaging system generally includes a pair of x-ray detectors (corresponding to the pair of x-ray sources) for detecting x-rays that have passed through the target, and an image processor for generating an image of the target using the detected x-rays.

In the illustrated embodiment, the system 200 further includes means for sensing the respiration of the patient and the pumping motion of the heart, and for generating a signal representative of the motion of the target due to respiration and heart beat of the patient. In the illustrated embodiment, the means for sensing the respiration is a breathing sensor 214, and the means for sensing the heart beat is a heart beat monitor 216. In other embodiments of the invention, the system 200 may include means for sensing other types of motion of the patient, for example motion due to pulsating arteries. The breathing sensor 214 may be coupled to an external body part of the patient that moves in synchronization with the respiration of the patient, and a sensor reader (not illustrated) may be provided that takes a reading from the breathing sensor periodically. A number of commercially available sensors may be used as the breathing sensor 214, including infrared tracking systems, force sensors, air flow meters, strain gauges, laser range sensors, and a variety of sensors based on physical principles such as haptic, acoustic/ultrasound, magnetic, mechanical or optical principles.

In the illustrated embodiment, the system 200 includes a signal processor 220 for processing the signal representative of the composite motion (due to both breathing and heartbeat) of the target region, to generate therefrom a first signal substantially characterized by a frequency F1 representative of the respiratory motion of the patient, and a second signal substantially characterized by a frequency F2 representative of the cardiac pumping motion. Appropriate processing units in the controller 208, together with the imaging means 206, are used to generate a first correction factor from the first signal, and a second correction factor from the second signal. The first correction factor, when applied to the controller subunit 300, is effective to move the robot (and hence the x-ray source) to adjust the relative position of the x-ray source and the target, in a way that accounts for movement of the target due to respiration of the patient. The second correction factor, when applied to the controller subunit 300, is effective to correct the relative position of the x-ray source and the target, to account for movement of the target due to cardiac pumping.

Figure 3B:
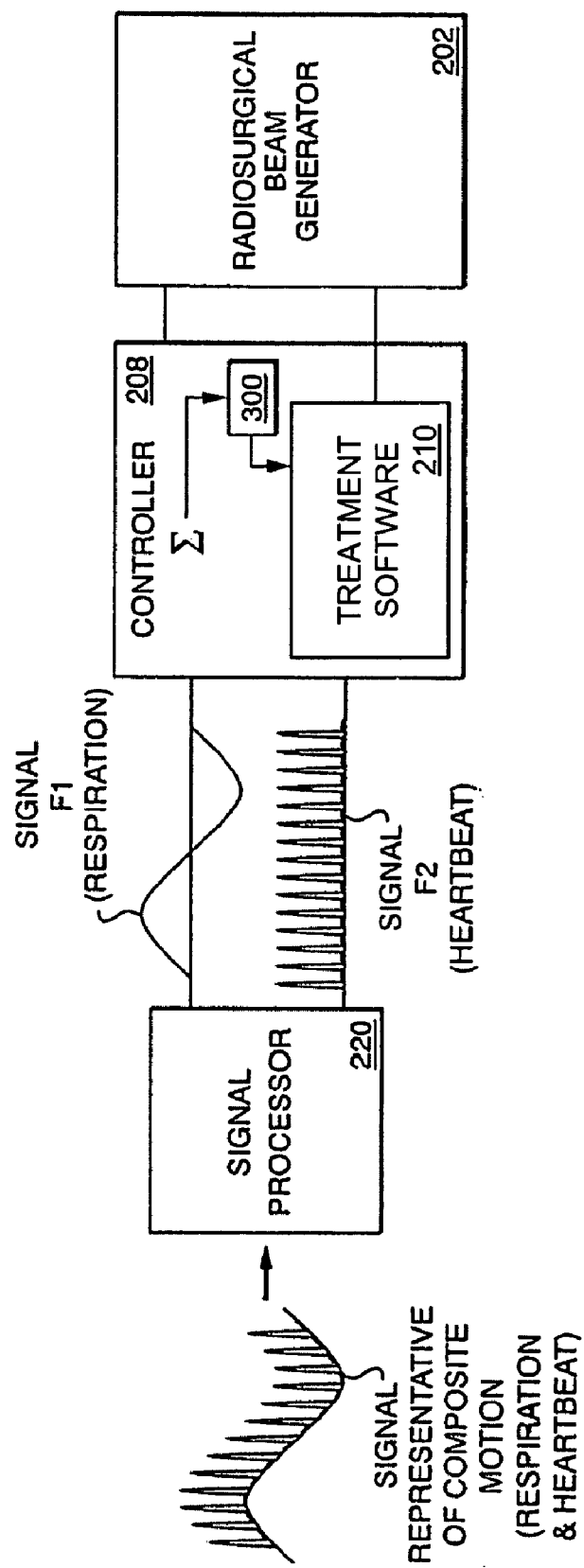
FIG. 3B schematically illustrates the splitting of the signal (representing the composite motion of the target region into first and second signals.

FIG. 3B schematically illustrates the splitting of the signal representing the composite motion of the target, into first (F1) and second (F2) signals, and the generation of the two correction factors. For example, the original signal (representing the composite motion) can be split into two signals, which are processed separately so as to eliminate a different one of the two components (F1 and F2). The processing could be done by filtering, by way of example. In a preferred embodiment, the original composite signal is treated as a signal plus out-of-band noise. The signal processor 220 may include noise canceling software for eliminating one or more undesired frequency components, i.e. out-of-band noise. For example, one or more conventional noise-canceling algorithms known in the art may be used to cancel the undesired component(s). By way of example, the noise canceling algorithms may be effective to extract the undesired component(s), and invert the extracted components. The algorithm may then generate one or more signals that cancel out the undesired frequency component(s).

The first and second correction factors are recombined, and superposed, resulting in a combined correction factor. The correction factor, when applied to the controller subunit 300, accounts for the composite motion of the target due to both breathing and heart beat.

Figure 4:
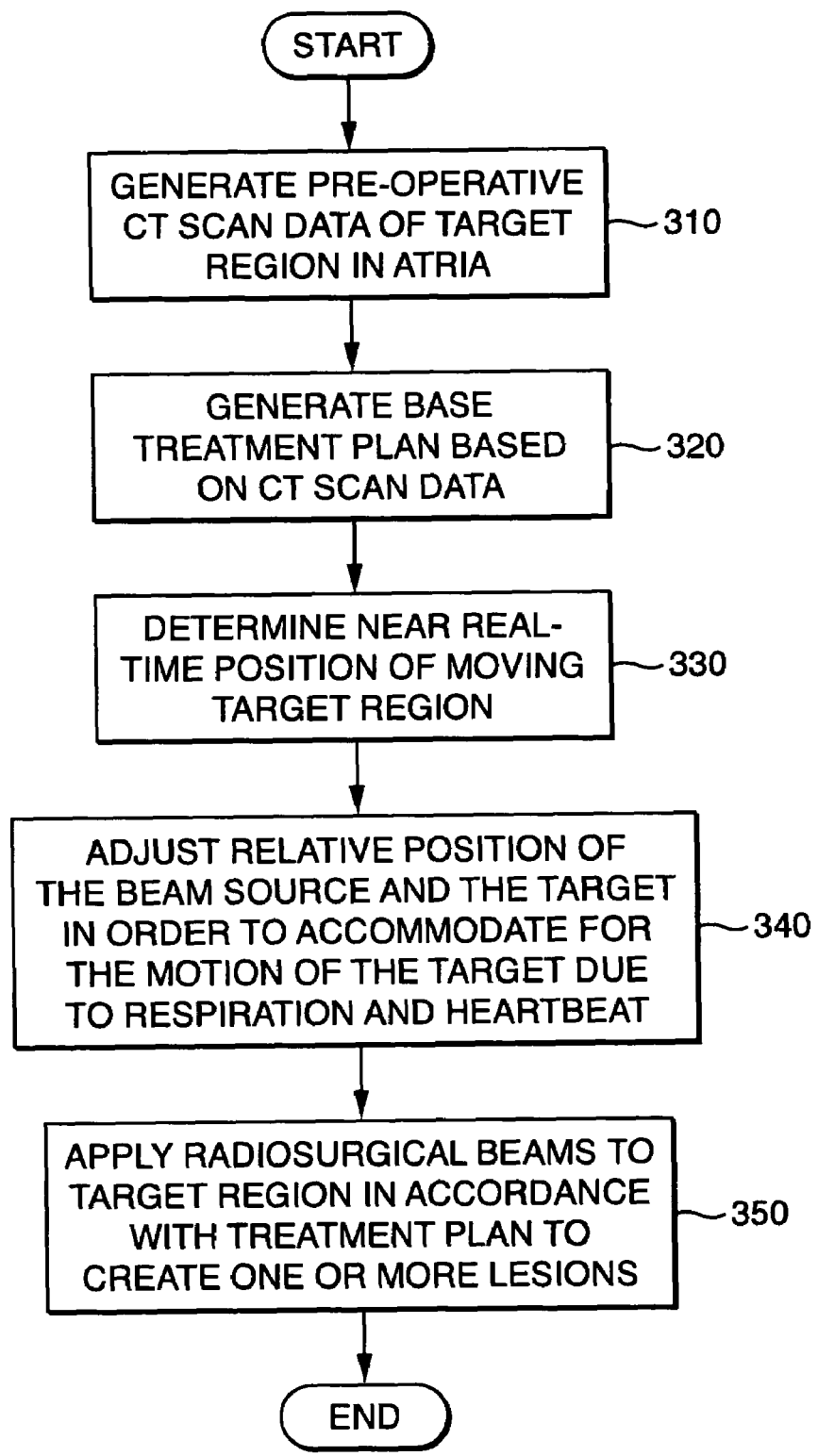
FIG. 4 provides a schematic flow chart of a method in accordance with the present invention.

FIG. 4 provides a schematic flow chart of a method in accordance with the present invention. In operation, CT scan data are generated in step 310. These data are representative of a pre-operative 3-D diagnostic image of the target. Because the target is a moving target, the diagnostic image may show the position of the target with respect to a plurality of fiducials. In the next step 320, a treatment plan is generated, based on the CT scan data generated in step 310. The treatment plan determines a succession of desired beam paths, each having an associated dose rate and duration, at each of a fixed set of locations.

In step 330, the position of the moving target is determined, in near real time. Next, in step 340, the relative position of the beam source 202 and the target is adjusted to accommodate for the change in the position of the target, i.e. the difference in the position of the target (e.g. determined relative to the fiducials) at the current time, compared to the position of the target in the pre-operative CT scan. Finally, in step 350 surgical x-rays are applied to the target in accordance with the treatment plan, thereby creating one or more lesions in the desired locations.

Because the target is always moving, the step of determining (in near real time) the position of the target includes the step of tracking the motion of the target. In one embodiment, the step of tracking the motion of the target includes generating at least one signal representative of the motion. In one embodiment, in order to track the motion of the target, the following steps may be taken: 1) the breathing sensor and the heart beat monitor are used to detect the respiration and the cardiac pumping of the patient, and record information relating thereto; 2) a plurality of x-ray images of the target and the implanted fiducials are generated in near real time; 3) the recorded information from the breathing sensor and the heart beat monitor are combined with the plurality of real-times x-ray images, thereby tracking the movement of the target (relative to the fiducials), as the patient breathes and the patient's heart beats.

In one embodiment, the signal representative of the composite motion of the target is split into two signals, and the two signals may be separately processed through a signal processor, in order to remove undesired frequency components from each signal. A first signal, substantially characterized by a frequency F1 (representing the respiratory cycle of the patient), and a second signal substantially characterized by a frequency F2 (representing the heart beat), are generated. A first correction factor is generated from the first signal (F1), and a second correction factor is generated from the second signal (F2).

In one embodiment of the invention, a look-up table of positional data may be established for a succession of points along each of the respiratory cycle and the heartbeat cycle, using techniques similar to those disclosed in the '981 patent. Motion points for the moving target include position information obtained in response to both respiration and heartbeat of the patient. Positional information for the heartbeat cycle can be obtained through imaging of the tissue while the patient is holding his breath. A table ("table 2") containing this positional information can provide the basis for the second signal. The second signal, on the other hand, can be obtained by subtracting data from the table for the heartbeat cycle (which was obtained by having the patient hold his breath) from the data from the composite motion (formed from both respiration and heartbeat), since the resulting table ("table 1") corresponds to motion caused substantially only by respiration. Positional changes for the x-ray source can be applied based on superposition of data from table 1 and table 2.

As explained earlier, the first correction factor accounts for the breathing motion, and the second correction factor accounts for the cardiac pumping motion. As mentioned earlier, the first and second correction factors are superposed, to generate a combined correction factor that can be applied to the controller subunit 300, so that the composite motion due to both respiration and heart beat can be accounted for.

In another embodiment, the step of generating the first and second correction factors may include the step of digitally comparing the plurality of near real-time x-ray images with the pre-operative CT diagnostic image. The digital comparison may be done, for example, by: 1) generating one or more DRRs (digitally reconstructed radiographs), using the pre-operative CT scan information together with the known imaging-beam positions, angles, and intensities; and 2) computing (using one or more processing units in the controller 208) the amount the target must be moved (translationally and rotationally) in order to bring the DRRs into registration with the real-time x-ray images. DRRs are artificial two-dimensional images, which show how an intermediate three-dimensional image would appear, if a hypothetical camera location and angle, as well as a hypothetical imaging beam intensity, were used. In other words, DRRs are synthetically constructed two-dimensional radiographs that are expected to result, if one or more imaging beams having a known intensity were directed to the target from certain known locations and angles. Algorithms known in the art, for example ray-tracing algorithms, are typically used to synthetically reconstruct the DRRs.

In one embodiment, the step of generating the requisite corrections (for adjusting the relative position of the x-ray source and the target, in near real time) to the command signals from the subunit 300 may include: 1) extrapolating the detected motion of the target into a complete cycle; and 2) synchronizing the command signals with the extrapolated motion of the target region, so as to modify the relative positions of the beam source and the target based on the extrapolated motion information. The changes in position of the target is constantly tracked over time, throughout the treatment period. The resulting modifications in the relative positions of the beam source 202 and the target are communicated to the beam source 202 and the positioning system 204 by the controller 208. As a result, the position, direction, and intensity of the radiosurgical beams are continuously adjusted, so that an accurate radiation dose can be applied to the appropriate regions of the patient's anatomy in accordance with the treatment plan, throughout the radiosurgical treatment. The plurality of radiosurgical beams remain directed to the target, in accordance with the treatment plan, throughout the duration of the treatment, and the radiosurgical x-ray beam source tracks the movement of the target.

As an improvement, instead of tracking the changes constantly over time, the system 200 can, for one component (for example, the lower frequency component F1 derived from the breathing motion), have a relatively static correction appropriate for just the "peak" of the respiratory cycle, in another embodiment of the present invention. In this embodiment, treatment by creating radiosurgical lesions may be performed only at the peaks of the respiratory cycle using the command signals modified by only the static correction factor (from breathing), and a dynamic (constantly monitored and changing) high-frequency correction factor, derived from heartbeat.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of treating a moving target in a patient by applying to said target one or more radiosurgical beams generated from a radiosurgical beam source, the method comprising:
    generating a pre-operative 3D scan of said target and of a surrounding region, said 3D scan indicating the position of said target relative to said surrounding region;
    based on said 3D scan, generating a treatment plan defining a plurality of radiosurgical beams appropriate for creating at least one radiosurgical lesion on said target;
    in near real time, detecting the motion of a target to determine the position of said target at a current time, and generating one or more signals representative of said motion of said target;
    in near real time based on the generated one or more signals, determining a difference in the position of said target at said current time, as compared to the position of said target as indicated in said 3D scan;
    in near real time, adjusting the relative position of said radiosurgical beam source and said target in order to accommodate for said difference, and applying x-rays to said target from said adjusted position of said radiosurgical beam source; wherein said motion of said target is a composite motion that is caused by a combination of:
    respiration of the patient; and
    pumping of the heart of the patient; and
    wherein generating one or more signals representative of said motion of said target comprises:
    establishing a look-up table of positional data for said composite motion of said data, by imaging said target and said surrounding region while the target undergoes said composite motion;
    establishing a look-up table of cardiac motion data for a succession of points along a heartbeat cycle of said patient, by imaging said target and said surrounding region while the patient is holding his breath;
    establishing a look-up table of respiratory motion data for a succession of points along a respiratory cycle of said patient, by subtracting said cardiac motion data from said positional data for said composite motion of said data;
    generating a first signal representative of the respiratory motion of patient from the data from said look-up table of respiratory motion, said first signal being characterized by a first frequency representative of the respiratory motion of said patient; and
    generating a second signal representative of the cardiac motion of said patient from the data from said look-up table of cardiac motion data, said second signal being characterized by a second frequency representative of the cardiac motion of said patient.

2. A method in accordance with claim 1, further comprising sequentially repeating detecting motion of said target and determining the difference in the position of said target during treatment, wherein said plurality of radiosurgical beams remain directed onto said target in accordance with said treatment plan throughout the duration of the treatment, and wherein said radiosurgical beam source tracks said movement of said target.

3. A method in accordance with claim 1, wherein said treatment plan comprises information regarding a number, intensities, positions, and directions of said plurality of radiosurgical beams that are effective to create said at least one lesion.

4. A method in accordance with claim 1, further comprising implanting a plurality of fiducials within said surrounding region proximate to said target, before taking said pre-operative 3D scan, wherein said position of said target as indicated in said pre-operative 3D scan is the position of the target relative to said plurality of fiducials.

5. A method in accordance with claim 1, wherein adjusting the relative position of said radiosurgical beam source and said target comprises:
    splitting said signal representative of said movement of said target into first and second signals;
    separately processing said first and second signals to remove undesired components from each signal, wherein processing said first and second signals comprises:
    generating a first processed signal substantially characterized by a first frequency representative of the respiratory motion of said patient, and a second processed signal substantially characterized by a second frequency representative of the pumping of the heart of said patient;
    generating from said first processed signal a first correction factor that is effective, when applied to a controller that controls the position of said radiosurgical beam source with respect to said target, to modify the position of said radiosurgical beam source relative to said target to account for the movement of said target due to respiration of said patient;
    generating from said second processed signal a second correction factor that is effective, when applied to said controller, to modify the position of said radiosurgical beam source relative to said target to account for the movement of said target due to the pumping of the heart of said patient;
    superposing said first and second correction factors, to generate a combined correction factor that is effective, when applied to said controller, to modify the position of said radiosurgical beam source relative to said target to account for said composite motion of said target region caused by both respiration and cardiac pumping.

6. A method in accordance with claim 5, wherein said first signal and said second signal are substantially decoupled and mutually orthogonal.

7. A method in accordance with claim 5, wherein processing said first and second signals comprises using an adaptive filter to filter out noise.

8. A method in accordance with claim 5, wherein processing said first and second signals comprise using one or more noise-canceling algorithms for eliminating one or more undesired frequency components.

9. A method in accordance with claim 8, wherein said one or more noise-canceling algorithms are effective to:
   extract said one or more undesired frequency components;
   invert said extracted frequency components; and
   generate one or more signals that cancels said one or more undesired frequency components.

10. A method in accordance with claim 5, wherein said respiratory motion is characterized by a respiratory cycle, and wherein said first correction factor is a relatively static factor that accounts for motion of said target during only a selected portion of said respiratory cycle.

11. A method in accordance with claim 10, wherein said selected portion of said respiratory cycle is centered about a peak within said respiratory cycle.

12. A method in accordance with claim 5, wherein generating said first correction factor comprises:
   digitally comparing said one or more near real-time x-ray images with said pre-operative 3D scan to compute the difference in position between the position of the target as indicated in the pre-operative 3D scan as compared to the position of the target in said near real-time x-ray images.

13. A method in accordance with claim 12, wherein digitally comparing said near real-time x-ray images comprises:
   generating one or more digitally reconstructed radiographs (DRRs) using the pre-operative 3D scan together with said known beam paths and intensities of said x-ray imaging beams;
   computing changes in position and orientation of said target in the one or more DRRs in order to bring said one or more DRRs in registration with said one or more real-time x-ray images.

14. A method of treating a moving target in a patient by applying one or more radiosurgical beams, generated from a radiosurgical beam source, to said target, the method comprising:
   generating a treatment plan containing information defining the positions, angles, and intensities of one or more radiosurgical beams that are adapted to create, when applied to said target, at least one radiosurgical lesion, said treatment plan being based on 3D scan data that indicates the position of said target at treatment planning time;
   in near real time, monitoring the motion of said target to determine the difference between the position of the target at a current time, as compared to the position of said target at treatment planning time as indicated by said 3D scan data;
   in near real time, adjusting the relative position of the radiosurgical beam source and said target to account for the difference in target position using a robotic controller; and
   applying one or more radiosurgical beams from said adjusted position of said radiosurgical beam source; and
   wherein said motion of said target is caused by the respiration and the heart beat of said patient; and wherein the adjusting said relative position of said radiosurgical beam source to account for the difference in target position comprises:
   sensing the motion of said target during a time interval, using a breathing sensor and a heart beat sensor;
   extrapolating said motion into a complete cycle; and
   synchronizing said robotic controller with said extrapolated motion of said target.

15. A system for treating a moving target in a patient by forming a radiosurgical lesion on said target, the system comprising:
   an apparatus for generating 3D scan data representative of a pre-operative 3D diagnostic image of said target and a surrounding region;
   a processor including treatment planning software for generating, based on said 3D scan data, a base treatment plan defining a plurality of x-ray beams appropriate for creating at least one lesion in said target;
   a beam source for generating one or more radiosurgical beams adapted to create at least one lesion in said target;
   a positioning system that controls the relative position of said beam source and said target;
   imaging means for generating at least one real-time x-ray image of said target;
   means for sensing the motion of said target, and for generating at least one signal representative of said motion; and
   means for generating from said at least one signal at least one correction factor that is effective, when applied to said positioning system, to modify the position of said beam source relative to said target to accommodate for the difference in position of said target at a current time as compared to the position of said target in said pre-operative diagnostic image;
   a signal processor coupled to the processor, the signal processor to process said at least one signal to generate a first signal substantially characterized by a first frequency, and a second signal substantially characterized by a second frequency;
   means for generating from said first signal a first correction factor, and for generating from said second signal a second correction factor; and
   means for superposing said first correction factor and said second correction factor to obtain said correction factor that is effective, when applied to said positioning system, to modify the position of said beam source relative to said target so as to accommodate for the difference in position of said target at a current time as compared to the position of said target in said pre-operative diagnostic image.

16. A system in accordance with claim 15, wherein said motion of said target is caused by respiration of said patient and by the pumping of the heart of said patient, and wherein said means for sensing the motion of said target includes a breathing sensor for sensing the respiration of said patient, and a heart rate monitor for monitoring the cardiac pumping of said patient.

17. A system in accordance with claim 15, wherein said first frequency is representative of the respiratory motion of said patient, and said second frequency is representative of the cardiac pumping motion of said patient.

18. A system in accordance with claim 15, wherein said first correction factor is a relatively static factor that accounts for motion of said target during only a portion of said respiratory cycle.

19. A system in accordance with claim 15, wherein said positioning system is an industrial robot having an articulated arm assembly, and wherein said radiosurgical beam source is an x-ray linac mounted at one end of said articulated arm assembly of said robot.

20. A system in accordance with claim 15, wherein said positioning system is effective, in response to receipt of said correction factor, to modify the position of said beam source in such a way that said radiosurgical beam source tracks the motion of said target.

21. A system in accordance with claim 15, wherein said imaging means comprises:
   one or more x-ray sources to generate x-ray imaging beams; and
   one or more corresponding x-ray detectors to detect said imaging beams after said imaging beams have traversed said target.

22. A system in accordance with claim 15 wherein said pre-operative 3D scan data comprise at least one of CT scan data; PET scan data; or MRI scan data.

23. A system in accordance with claim 15, wherein said means for generating said first correction factor comprises means for digitally comparing said one or more near real-time x-ray images with said pre-operative 3D scan to calculate the difference in position between the position of the target as indicated in the pre-operative 3D scan as compared to the position of the target in said near real-time x-ray images.

24. A system in accordance with claim 23, wherein said means for digitally comparing said one or more near real-time x-ray images with said 3D scan comprises:
   means for generating one or more DRRs using the 3D scan together with information regarding the beam paths and intensities of said x-ray imaging beams; and
   computing the changes in position and orientation of said target that are necessary in order to bring said one or more DRRs in registration with said one or more real-time x-ray images.

25. A system in accordance with claim 15, wherein said signal processor comprises:
   means for splitting said at least one signal into first and second signals;
   means for processing said first and second signals to remove undesired components from each signal, so as to generate said first signal substantially characterized by a first frequency, and said second signal substantially characterized by a second frequency.

26. A system in accordance with claim 25, wherein said means for processing said first and second signals comprises an adaptive filter for filtering out noise.

27. A system in accordance with claim 25, wherein said means for processing said first and second signals comprises software that includes one or more noise-canceling algorithms for eliminating one or more undesired frequency components, and wherein said one or more noise-canceling algorithms are effective to:
   extract said undesired frequency components;
   invert said extracted frequency components; and
   generate one or more signals that cancel said undesired frequency components.

* * * * *